United States Patent [19]

Courty et al.

[11] Patent Number: 4,675,343

[45] Date of Patent: Jun. 23, 1987

[54] PROCESS OF USE OF A CATALYST FOR SYNTHESIZING SATURATED PRIMARY ALIPHATIC ALCOHOLS

[75] Inventors: Philippe Courty, Houilles; Daniel Durand, Rueil-Malmaison; Alain Forestiere, Vernaison; Pierre Grandvallet, Rueil-Malmaison, all of France

[73] Assignee: Institut Francais du Petrole, Rueil-Malmaison, France

[21] Appl. No.: 863,283

[22] Filed: May 15, 1986

[30] Foreign Application Priority Data

May 17, 1985 [FR] France .................................. 85 07581

[51] Int. Cl.⁴ .............................................. C07C 27/06
[52] U.S. Cl. ..................................... 518/713; 518/709
[58] Field of Search ................................ 518/713, 709

[56] References Cited

U.S. PATENT DOCUMENTS 4,477,594 10/1984 Greene et al. ...................... 518/713

Primary Examiner—Howard T. Mars
Attorney, Agent, or Firm—Millen & White

[57] ABSTRACT

The present invention concerns a process of use of a copper and cobalt-containing catalyst for synthesizing saturated primary aliphatic alcohols. This process comprises a first step consisting in at least one catalyst prereduction by means of a gas mixture containing a reducing compound, a second step wherein the prereduced catalyst is contacted with a mixture of hydrogen and carbon oxides (CO, $CO_2$) for at least 10 hours, so as to produce a mixture of alcohols; a third step wherein the catalyst obtained in the second step is subjected to a treatment with a gas mixture containing a single reducing gas, during about 1 to 400 hours and a fourth step of synthesizing saturated primary aliphatic alcohols from a mixture containing hydrogen and carbon oxides.

Optionally the process also comprises an additional step consisting of subjecting the catalyst, whose activity and/or selectivity has been partially lost, to a new treatment according to the procedure defined for the third step.

The process according to the invention is particularly applicable to catalysts containing copper, cobalt and optionally aluminum and/or zinc and/or sodium.

10 Claims, No Drawings

PROCESS OF USE OF A CATALYST FOR SYNTHESIZING SATURATED PRIMARY ALIPHATIC ALCOHOLS

The present invention relates to a catalytic process for the synthesis of primary alcohols, particularly higher alcohols, by reaction of carbon oxides (CO, $CO_2$) with hydrogen. The obtained alcohols are mainly saturated primary aliphatic alcohols having two or more carbon atoms. Generally, a mixture of alcohols is obtained which contains a high proportion of $C_2$–$C_6$ alcohols.

The present invention concerns more particularly an improved process of use of catalysts for synthesis of alcohols from synthesis gas. The catalysts used according to the present invention are particularly those containing copper and cobalt and, optionally and often advantageously, at least one alkali or alkaline-earth metal and/or zinc, such for example as those disclosed in the U.S. Pat. Nos. 4,122,110, 4,291,126 and 4,346,179, in the French patent application No. 2 523 957 and 2 543 945 and in the French patent application No. 2 564 091.

BACKGROUND OF THE INVENTION

Various processes of use of copper and cobalt catalysts have been disclosed in the patent literature. In the process for synthesizing alcohols according to U.S. Pat. No. 4,122,110, the catalysts are directly placed into the synthesis gas.

According to the process disclosed in the French patent application No. 2 523 957, the catalysts are preliminarily reduced. This reduction may be achieved, according to this patent, for example in a single step, by means of a mixture of inert gas with at least one reducing compound, in a molar ratio "reducing gas/reducing gas+inert gas" from 0.001:1 to 1:1, the reducing gas being selected from the group consisting of hydrogen, carbon monoxide, $C_1$ and $C_2$ alcohols and aldehydes, the reduction being performed at a temperature from 100° to 750° C., preferably from 150° to 550° C. and, for example, by 10-hour steps from 170° C. to 240° C., under a pressure from 0.1 to 10 megapascals (MPa), preferably 0.1–6 MPa and for example at atmospheric pressure (0.1 MPa).

Another method of preliminary reduction of the catalysts according to this patent application consists of proceeding in at least two successive steps. In this embodiment, the first reduction step is conducted at a temperature from 150° to 250° C. with a molar ratio "reducing gas/reducing gas+insert gas" from 0.001:1 to 0.1:1, said first step being continued until the concentrations of reducing gas at the input and the output of the reactor be the same.

Then, in a second step, the temperature is increased up to a value ranging from 220° to 750° C., preferably from 240° to 550° C., the molar ratio "reducing gas/reducing gas+inert gas" being from 0.01:1 to 1:1. During said second step, it is generally advantageous to use a higher concentration of reducing gas than in the first step.

Another process of use of catalysts for synthesizing alcohols, particularly higher alcohols, has been disclosed in U.S. Pat. No. 4,477,594.

The process disclosed in this patent concerns the use of catalysts for synthesizing $C_2$–$C_9$ saturated aliphatic alcohols from synthesis gas, said catalysts comprising oxides of copper, zinc, aluminum, potassium and one or two metals selected from the group consisting of chromium, manganese, cerium, cobalt, thorium and lanthanum.

This process comprises a first step of partial activation of the catalyst by contacting said catalyst with a gas stream comprising hydrogen and at least one inert gas, said gas stream having a space velocity up to 5000 liters per hour and per kilogram of catalyst; a second activation step wherein the catalyst obtained in the first step is contacted with hydrogen and carbon monoxide, the $H_2$/CO volume ratio being from 0.5:1 to 4:1, the temperature from 200° to 450° C. and the pressure from 35 to 200 atmospheres, said $H_2$+CO mixture having a space velocity from 1000 to 20 000 liters per hour and per kilogram of catalyst and said second step being continued until at least 500 000 liters of gas per kilogram of catalyst have been in contact with said catalyst; a third step of synthesizing saturated aliphatic alcohols, consisting of contacting the activated catalyst obtained at the end of the second step with a synthesis gas containing hydrogen and carbon monoxide in a ratio by volume from 0.5:1 to 4:1, at a space velocity from 1 000 to 20 000 liters per hour and per kilogram of catalyst, at a temperature from 200° to 450° C. and under a pressure from 35 to 200 atmospheres (3.5 to 20 MPa).

This patent thus discloses a process wherein the catalyst is subjected to a reduction with a gas mixture containing hydrogen and an inert gas and then to the synthesis conditions. Then only after a certain operating period is the catalyst employed to obtain products. The use of the catalysts according to one of the above-described methods, however, does not always provide for a satisfactory selectivity by weight to alcohols $S.C_2$+OH (alcohols having 2 carbon atoms or more) and/or a sufficient selectivity to total alcohols (SA) and/or an acceptable productivity by weight.

According to the present invention, a new procedure has been discovered for using catalyst for synthesizing higher saturated aliphatic alcohols, said procedure providing mostly for a substantial increase in one or more of the deserved relationships performances of the reaction: weight productivity (P) to alcohols, selectivity ($S_A$) to total alcohols, and selectivity by weight to higher alcohols ($S.C_2$+OH).

The process according to the present invention also provides, in particular, for at least a partial improvement of the selectivity and/or productivity of a catalyst used over a relatively long period and whose activity, at the end of this operating period, is decreased as compared with its initial activity and/or whose selectivity decreases in such proportions that it is no longer possible to continue the synthesis under acceptable economic conditions and/or the desired products are no longer formed in sufficient proportions.

The process according to the invention thus avoids the need to replace the used catalyst with a fresh catalyst. A satisfactory selectivity and/or activity is restored to the used catalyst according to the present invention. Thus the used catalyst may continue to be used over a new operating period.

SUMMARY OF THE INVENTION

The process according to the present invention for synthesizing saturated primary aliphatic alcohols by reaction of carbon oxides (CO, $CO_2$) with hydrogen, in the presence of a copper and cobalt-containing catalyst, comprises:

a first step consisting of at least one prereduction of the catalyst by means of a gas mixture containing a reducing compound, a second step wherein the prereduced catalyst obtained in the first step is contacted with a mixture of hydrogen and carbon oxide (CO, $CO_2$), under conditions providing for the synthesis of a mixture of saturated primary aliphatic alcohols containing higher alcohols, for about at least 10 hours, a third step wherein the catalyst obtained in the second step is subjected to a treatment with a gas mixture containing a single reducing gas, a fourth step of synthesizing a mixture of saturated primary aliphatic alcohols containing higher alcohols from a mixture of hydrogen and carbon oxides (CO, $CO_2$).

In the first step of the process the catalyst is subjected to at least one prereduction, said prereduction being performed by contacting the catalyst with a gas mixture containing at least one inert gas and at least one reducing gas, in a molar proportion "reducing gas/reducing gas+inert gas" of about 0.001:1 to 1:1 and preferably about 0.01:1 to about 0.1:1, said reducing gas being selected from the group formed of hydrogen and carbon monoxide and advantageously consisting of hydrogen. The inert gas may be any inert gas or gas mixture well known in the art, not reacting in the prereducing conditions. Nitrogen is used for example. Said first step is most often performed at a temperature of about 100° to about 750° C., preferably about 120° to about 600° C. and, more preferably, about 120° to about 250° C., under a total pressure from about 0.1 to about 10 megapascals (MPa), preferably about 0.1 to about 6 MPa, with a partial pressure of the reducing gas at most equal to about 1 MPa and with a volume velocity per hour (VVH) of the gas mixture from about $10^2$ to about $4.10^4$ hour$^{-1}$ and preferably from about $5.10^2$ to about $2.10^4$ hour$^{-1}$. This first step of the process is generally performed for a sufficient time to obtain the same concentration of reducing gas at the input and at the output of the reactor.

This first step may thus consist in a single prereduction in the above conditions or, for example, under two successive prereductions, the first prereduction being then preferably conducted in the following conditions:

temperature of about 120° to about 250° C.,
total pressure from about 0.1 to about 10 MPa,
partial pressure of the reducing gas lower than or equal to about 1 MPa,
VVH of about $10^2$ to about $4.10^4$ hour$^{-1}$,
molar ratio "reducing gas/reducing gas+inert gas" from about 0.001:1 to 0.1:1, said first prereduction being continued for a sufficient time to obtain the same concentrations of reducing gas at the input and at the output of the reactor (thus showing that the first prereduction step is completed).

This first prereduction is performed with a reducing gas selected from the group consisting of hydrogen and carbon monoxide, said reducing gas being preferably hydrogen. The second prereduction step is then conducted in the following conditions:

temperature from about 220° to about 750° C., preferably from about 240° to about 600° C.;
molar ratio "reducing gas/reducing gas+inert gas" from about 0.01:1 to 1:1.

The pressure and hourly volume velocity remain within the ranges mentioned above for the first prereduction. The reducing gas and the inert gas are advantageously the same as those used in the first prereduction step. This second prereduction step is conducted under more severe conditions, as a whole, than the first prereduction. It may be advantageous in said second prereduction step to increase the temperature and also, optionally, the concentration of the reducing gas. At least one of the factors of said second prereduction is so selected as to obtain an increased reduction of the catalyst as compared with that obtained during the first prereduction step. Said second prereduction is generally continued over a sufficient time to obtain the same concentration of reducing gas at the input and at the output of the reactor (thus showing that the second prereduction is completed). The second step of the present process consists of contacting the prereduced catalyst obtained at the end of the first step with a synthesis gas containing hydrogen and carbon oxides (CO, $CO_2$) in a molar ratio $H_2/CO+CO_2$ from about 0.4 to about 10, preferably from about 0.5 to about 4, under a total pressure from about 2 to about 15 MPa, preferably from about 5 to about 10 MPa, and with a partial pressure of the hydrogen-carbon monoxide mixture of at least about 2 MPa, at a temperature from about 240° to about 350° C., preferably from about 240° to about 310° C., with a volumetric velocity per hour (VVH) from about $15.10^2$ to about $6.10^4$ hour$^{-1}$ and preferably from about $3.10^3$ to about $4.10^4$ hour$^{-1}$ for at least about 10 hours and preferably about 50 to 1000 hours, more preferably about 100-500 hours. Said second step is conducted so as to obtain a mixture of saturated primary aliphatic alcohols containing higher alcohols, i.e. alcohols having two or more carbon atoms in their molecule.

According to an alternative embodiment of the process, this second step is continued until the catalyst has lost at least a part of its productivity and/or selectivity to alcohols and/or selectivity to higher alcohols (having two or more carbon atoms).

The third step of the process consists of replacing the synthesis gas with a gas mixture containing a single reducing gas so as to subject the catalyst obtained in the second step to a treatment with said single reducing gas.

During said third step the catalyst obtained in the second step, is contacted with a gas mixture containing a single reducing gas and at least one inert gas, said single reducing gas being selected from the group consisting of hydrogen and carbon monoxide and being preferably hydrogen, said treatment being conducted at a temperature from about 200° to 750° C., preferably from about 240° to about 600° C., for a period from about 1 hour to about 400 hours, preferably from about 10 hours to about 200 hours and advantageously from about 20 hours to about 100 hours, under a pressure from about 0.1 to about 10 MPa, preferably from about 0.1 to about 6 MPa, with a volumetric velocity per hour (VVH) from about $10^2$ to about $4.10^4$ hour$^{-1}$, preferably from about $5.10^2$ to about $2.10^4$ hour$^{-1}$. During said third step, the molar ratio "single reducing gas/single reducing gas+inert gas" is about from 0.01:1 to 1:1, preferably about from 0.02:1 to 1:1.

The fourth step of the process is the step of synthesizing a mixture of saturated primary aliphatic alcohols containing higher alcohols.

During said step, the catalyst obtained in the third step is contacted with a synthesis gas containing hydrogen and carbon oxides (CO, $CO_2$) in a molar ratio $H_2/CO+CO_2$ from about 0.4 to about 10 and preferably from about 0.5 to about 4, at a pressure from about 2 to about 25 MPa, preferably from about 5 to about 15 MPa, with a volume velocity per hour (VVH) from about $15.10^2$ to about $6.10^4$ hour$^{-1}$ and preferably from about $2.10^3$ to about $2.10^4$ hour$^{-1}$, at a temperature from about 240° to about 400° C., preferably from about 240° to about 350° C.

The process according to the invention also comprises optionally an additional step wherein the used catalyst for synthesizing saturated primary aliphatic alcohols, recovered at the end of the fourth step after a relatively long running period of generally more than 1000 hours and which has at least partially lost its selectivity to alcohols and/or its selectivity to higher alcohols and/or its productivity to alcohols, is contacted with a gas mixture containing a single reducing gas and at least one inert gas (said single reducing gas being preferably hydrogen) under the conditions mentioned above for the third step, then used in a new synthesis step under the above-defined conditions, for the fourth step.

During this additional step of treatment with a single reducing gas as well as, sometimes, during the third step of the process of the present invention, methane formation may be observed occasionally. Without being bound by any theory, it is assumed that the methane formation originates from the reaction of hydrogen with carbon compounds occasionally accumulated on the active surface of the catalyst during the second step of during the fourth step of the present process.

The process of the present invention based on the use of copper and cobalt-containing catalysts for synthesizing saturated primary aliphatic alcohols may be applied with particular success to the catalysts disclosed in U.S. Pat. Nos. 4,122,110, 4,291,126 and 4,346,179; this process is well adapted to the use of the copper and cobalt catalysts disclosed in French patent application Nos. 2 523 957 and 2 543 945 and in French patent application No. 2 564 091, the descriptions of which are incorporated herein by way of reference and whose essential information is reproduced hereinafter: the catalysts to which the present process is applicable with a particular efficiency are those essentially containing copper, cobalt and optionally aluminum and/or zinc and/or one alkali or alkaline-earth metal (A) selected from the group formed of Li, Na, K, Rb, Cs, Be, Mg, Ca, Sr and Ba.

The alkali and/or alkaline-earth metals preferably used are Na, K, Mg, Ca and/or Ba.

Optionally the catalyst may further contain at least one metal M selected from the group consisting of manganese, iron, vanadium and rhenium. It may also optionally contain at least one metal N selected from the group consisting of scandium, yttrium, thorium, zirconium and the rare-earth metals of atomic numbers from 57 to 71 included, as well as optionally chromium in a low proportion.

These different metals are in the following proportion (in metal % by weight with respect to the total of metals

| Metal | Wide range | Preferred range | More preferred range |
|---|---|---|---|
| Copper | 8–70 | 10–65 | 20–50 |
| Cobalt | 3–55 | 5–50 | 9–40 |
| Aluminum | 0–45 | 5–40 | 7–30 |
| Zinc | 0–70 | 5–50 | 5–40 |
| A metal | 0–18 | 0–15 | 0.2–10 |
| M metal | 0–20 | 0–10 | 0.5–7 |
| N metal | 0–60 | 0–50 | 6–42 |

| Metal | Wide range | Preferred range | More preferred range |
|---|---|---|---|
| Chromium | 0–15 | 0–10 | 0.5–7 |

In addition, inside the above mentioned composition ranges by weight, the different metals are advantageously used in the following relative atomic proportions:

| Atomic ratio | Wide range | Preferred range | More preferred range |
|---|---|---|---|
| Cu/Co | 0.05–10 | 0.1–5 | 0.5–4.5 |
| Al/Co | 0–5 | 0.7–4 | 0.9–3.5 |
| A metal/Co | 0–3.5 | 0.05–1.5 | 0.08–0.75 |
| Zn/Co | 0–10 | 0.1–5 | 0.2–1.2 |
| M metal/Co | 0–1 | 0.002–0.5 | 0.005–0.2 |
| Cr/Co | 0–1 | 0.002–0.5 | 0.005–0.3 |
| N metal/Co | 0–2 | 0.02–1.5 | 0.04–1 |

When the catalyst contains aluminum and at least one M metal and/or chromium and/or N metal, the atomic proportions of these metals are preferably as follows:

M metals/Al=0.001–0.3, preferably 0.005–0.2
Chromium/Al=0.001–0.3, preferably 0.005–0.2
N metals/Al=0.05–1.5, preferably 0.08–1

Still optionally, the catalyst may contain 0 to 0.8% by weight, preferably 0.02 to 0.8% by weight of a noble metal from the platinum family (group VIII), more particularly palladium, rhodium and ruthenium.

EXAMPLES

The following examples describe different aspects of the invention and must not be considered as limiting the scope thereof. Example 1 concerns the preparation of a synthesis catalyst which is used in examples 2 to 5, illustrating the invention.

The results are defined as follows:

productivity by weight to alcohols (P): defined as the number of grams of alcohols obtained per hour, in proportion to the weight (in grams) of the charged catalyst.

selectivity by weight to higher alcohols $S_{C2}+OH$, defined as the the ratio by weight "$C_2+OH$ alcohols/total formed alcohols" $\times 100$, selectivity ($S_A$) in the conversion of CO and $CO_2$ to alcohols: $C_1OH, C_2OH, C_3OH, C_4OH \ldots C_nOH$ being the number of formed gram-molecules of each alcohol, the number $N_C$ of (CO+$CO_2$) gram-molecules converted to alcohols is:

$$N_C = C_1OH + 2C_2OH + 3C_3OH + 4C_4OH + \ldots + nC_nOH$$

The selectivity $S_A$ is given by the formula:

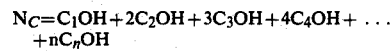
$$S_A = 100 \times \frac{N_C}{g.mol.(CO + CO_2)_{input} - g.mol.(CO + CO_2)_{output}}$$

(the reaction by-products are methane, $C_2+$ hydrocarbons as well as certain oxygenated compounds such as aldehydes, esters and ketones, present as traces).

EXAMPLE 1

Preparation of a catalyst containing copper, cobalt, aluminum, zinc and sodium.

338.24 g of trihydrated copper nitrate (1.4 g.at Cu), 101.86 g of hexahydrated cobalt nitrate (0.35 g.at Co), 450.2 g of hexahydrated aluminum nitrate (1.2 g.at Al)

and 178.5 g of hexahydrated zinc nitrate (0.6 g.at Zn) are dissolved in 4 l of distilled water. The solution is diluted up to 8 liters (solution A, 0.444 g.at/l), then brought to 70° C.

Separately, 602.0 g of sodium carbonate are dissolved in 3 liters of distilled water; the solution is diluted up to 9 liters (solution B, 1.26 g.at Na/l), then brought to 70° C. A heated reactor of 25 liters capacity, containing 5 liters of distilled water, alkalized to pH=8 and brought to 70° C., is fed simultaneously with solutions A and B for 2 hours, the flow rates being regulated by the pH which varies between 6.90 and 7.10. The resultant precipitate, after three washes with 15 liters of distilled water, contains 30% by weight of oxides of non-alkali metals and 0.05% by weight of sodium, in proportion to the oxides.

834 g of wet precipitate are contacted with 3 liters of a solution containing 54.45 g of sodium carbonate. After 30 minutes of strong stirring, the precipitate is again filtered (wet precipitate of 30% oxide content), dried in a ventilated stove for 16 hours at 80° C., then 3 hours at 100° C., then activated in air for 4 hours at 350° C.

The powder obtained by crushing to particles of less than 0.5 mm is admixed with 2% by weight of graphite, pelletized and then activated in air for 3 hours at 350° C.

The catalyst has the following atomic composition:

$$Cu_{1.4}Co_{0.35}Al_{1.2}Zn_{0.6}Na_{0.2}O_{4.425}$$

The composition by weight, in metal % by weight with respect to the total metals weight is: Cu: 47.88%; Co: 11.10%; Al: 17.43%; Zn: 21.11%; Na: 2.47%

The atomic ratios are: (Cu/Co)=4; (Al/Co)=3.43; (Zn/Co)=1.71 (Na/Co)=0.57

EXAMPLE 2 (comparative)

A tubular reactor of 2.5 cm diameter and 2 meters height is charged with about 500 g of the catalyst of example 1.

The reactor, initially under atmospheric pressure, is fed with nitrogen at a rate of 1500 liters/liter of catalyst per hour (l/l/h), under atmospheric pressure (0.1 MPa). The temperature is progressively brought to 130° C. When this temperature is reached, nitrogen is replaced with a hydrogen-nitrogen mixture containing 2% by volume of hydrogen, while maintaining the flow rate and increasing the temperature, by ten-hour steps at 130°, 150°, 170°, 190°, 210° and then 240° C. After 10 hours at 240° C. under the above-mentioned conditions the reactor is purged, then pressurized with nitrogen at 6 MPa. Nitrogen is then replaced with a synthetic gas $H_2+CO+CO_2$ having a $H_2/CO$ molar ratio of 2 and containing 2% of $CO_2$, while maintaining the temperature at 240° C. and the pressure at 6 MPa. The temperature is progressively increased up to 290°-300° C.; the pressure is maintained at 6 MPa and the flow rate of synthesis gas is of 3000 liters/liter of catalyst per hour (l/l/h). The contact between the catalyst and the synthesis gas is maintained under these conditions for about 200 hours. The results achieved by of the catalyst after 200 hours of run are as follows:

- selectivity to alcohols: $S_A=80\%$
- alcohols productivity by weight: P=0.10 g/h/g of catalyst
- selectivity by weight to higher alcohols $C_2+OH$: $S_{C_2}+OH=10\%$ The synthesis is continued up to 400 hours, the results at 400 hours being as follows:

$S_A=80\%$ P=0.08 g/h/g $S_{C_2}+OH=10.2\%$

EXAMPLE 3

A new test is conducted with a new charge of the catalyst of example 1, according to the process described in example 2. After 200 hours of the run, the reactor temperature is decreased to about 240° C., the pressure to 1 atmosphere (0.1 MPa) and the reactor is purged with nitrogen. Pure hydrogen is then introduced under atmospheric pressure at the rate of 500 liters per liter of catalyst and per hour and then the temperature is progressively increased up to 300° C. and then by two-hour steps, to 300° C., 400° C., 500° C., 530° C. After the 530° C. step the temperature is decreased to about 240° C., still under hydrogen and at atmospheric pressure.

The reactor is then purged with nitrogen, then pressurized with nitrogen at a pressure of 6 MPa. A synthesis gas is then introduced which has the same composition as that of the synthesis gas used in example 2; the temperature is increased up to 290°-300° C.; the pressure is maintained at 6 MPa and the flow rate of synthesis gas is 3000 l/l/h. This synthesis step is performed during 1000 hours. The performances at 100 hours, 200 hours and 1000 hours are given below:

| Time in hours | $S_A$ % | P g/h/g | $S_{C_2}+$ OH % |
|---|---|---|---|
| 100 | 72.1 | 0.071 | 30.5 |
| 200 | 72.4 | 0.070 | 30.3 |
| 1000 | 71.5 | 0.067 | 30.1 |

It is apparent that the process for using catalysts according to the invention provides for a very substantial increase of the selectivity by weight to higher alcohols ($S_{C_2}+OH$).

The step of treatment with pure hydrogen, described in the above example, may be replaced with a treatment by means of a gas mixture containing hydrogen and an inert gas, for example, nitrogen. The hydrogen partial pressure within the mixture may be higher than the atmospheric pressure (0.1 MPa). The hydrogen partial pressure may be for example from 0.101 to 3 MPa without resulting in very different results as compared with a treatment performed with pure hydrogen or hydrogen diluted in an inert gas with a hydrogen partial pressure of 0.1 MPa.

The intermediate step of purging with nitrogen before treatment with pure hydrogen, as above described, is optional. Similarly, the application of a nitrogen pressure after the treatment with pure hydrogen, as above described, is optional and it is possible to directly introduce the synthesis gas immediately after the treatment with hydrogen.

EXAMPLE 4 (comparative)

A catalyst charge having the same characteristics as that of example 1 is introduced into a tubular reactor, then reduced in two steps according to the following procedure:

First step: $H_2$ at 2% concentration in nitrogen
VVH=1500 h$^{-1}$
Temperature: 10-hour steps at 130°-150°-170°-190°-210° and 240° C.
Atmospheric pressure (0.1 MPa)
Second step: $H_2$ at 10% concentration in nitrogen
VVH=1500 h$^{-1}$ Temperature increased to 300° C., followed with 2-hour steps at 300°, 400° and 500° C.
Atmospheric pressure (0.1 MPa)

After the second step, the reactor is brought back to a temperature of about 240° C. and filled with synthesis gas ($H_2/CO=2$), P=6 MPa, VVH=3000 $h^{-1}$, and the temperature is brought to 290° C. The catalyst is operated for 400 hours under these conditions.

The performances at 100, 200 and 400 hours are given below:

| Time in hours | $S_A$ % | P g/h/g | $S_{C_2^+\text{ OH}}$ % |
|---|---|---|---|
| 100 | 61 | 0.065 | 41 |
| 200 | 55.6 | 0.067 | 40.2 |
| 400 | 51.2 | 0.061 | 39.7 |

EXAMPLE 5

A new test is conducted with a new charge of the catalyst of example 1, according to the procedure described in example 4. After 200 hours of the run, the reaction temperature is decreased to about 240° C., the pressure to 1 atmosphere and pure hydrogen is then introduced under atmospheric pressure (0.1 MPa) at a rate of 500 l/l/h. The temperature is increased up to 300° C. and then by 2-hour steps at 300° C.–400° C.–500° C. After the 500° C. step, the temperature is decreased to 240° C. and the reactor is pressurized at 6 MPa with synthesis gas ($H_2/CO=2$), and the synthesis is performed during 200 hours under the following conditions:

P=6 MPa; $H_2/CO=2$; VVH=3000 $h^{-1}$; T=290° C.

The performance at 100 and 200 hours are given below:

| Time in hours | $S_A$ % | P g/h/g | $S_{C_2^+\text{ OH}}$ % |
|---|---|---|---|
| 100 | 62.1 | 0.056 | 38.5 |
| 200 | 62.3 | 0.057 | 38.6 |

A comparison of the above results with those of example 4 shows that a catalyst used according to the process of the invention has a clearly improved stability of the selectivity to alcohols for a very close productivity and selectivity by weight to higher alcohols. The test has been continued up to 1000 hours without showing substantial variations in performance.

EXAMPLE 6

A catalyst of formula $Cu_{1.2} Co_{0.3} Al_{1.1} Zn_{0.7} Na_{0.2} O_{4.1}$ prepared according to the method described in example 1, is reduced according to the procedure described in example 3. After reduction at 530° C., the catalyst is placed in a synthesis gas under the following conditions:

P=6 MPa, VVH=3000 $h^{-1}$, T=300° C., $H_2/CO=2$

The results at 200, 500 and 4000 hours are given below:

| Time in hours | $S_A$ % | P g/h/g | $S_{C_2^+\text{ OH}}$ % |
|---|---|---|---|
| 200 | 63.3 | 0.074 | 39.2 |
| 500 | 63.2 | 0.071 | 39.2 |
| 4000 | 62.1 | 0.059 | 38.8 |

After 4000 hours, the productivity was decreased by about 20%. The catalyst was then placed under hydrogen according to the following procedure:

The temperature and pressure of the reactor are respectively decreased to 280° C. and 10 atmospheres (1 MPa) and then the whole flow of carbon monoxide and a part of the hydrogen flow are very quickly replaced with a nitrogen flow so that the hydrogen partial pressure in the hydrogen-nitrogen gas mixture be about 0.1 MPa. A gas flow of 1000 l/l/h is maintained for about 10 hours under these conditions of temperature and pressure. The temperature is then progressively increased to 500° C. by 10-hour steps at 300°, 350°, 400°, 450° and 500°. C. The reactor is then brought back to 280° C., purged with nitrogen, then pressurized with nitrogen at 6 MPa. Nitrogen is then replaced with the synthesis gas ($H_2/CO=2$) and the reactor is brought to 300° C. The synthesis is then performed for 1000 further hours in the following conditions:

P=6 MPa; T=300° C.; VVH=3000 $h^{-1}$; $H_2/CO=2$

The results at 100, 500 and 1000 hours are given below:

| Time in hours | $S_A$ % | P g/h/g | $S_{C_2^+\text{ OH}}$ % |
|---|---|---|---|
| 100 | 66.5 | 0.069 | 35.4 |
| 500 | 66.3 | 0.065 | 35.6 |
| 1000 | 65.8 | 0.063 | 35.2 |

It is observed that the so-treated catalyst has a clearly improved productivity (P): increased up to about 93% of the initial productivity.

EXAMPLE 7 (comparison)

In order to better show the advantage of the catalyst treatment with hydrogen after a long period of operation, a new test according to the procedure described in example 6 has been performed with the catalyst described in example 6, over 5000 hours and without proceeding to a treatment at 4000 hours.

The performance obtained at 5000 hours is as follows:

$S_A=61.7\%$; P=0.05 g/h/g; $S_{C_2^+\text{OH}}=38.3\%$

EXAMPLE 8 (comparative)

A catalyst of formula $Cu_1 Co_{0.3} Zn_{1.2} K_{0.02} O_{2.66}$ is prepared according to the method described in example 1, with the exceptions that the nitrate solution contains no aluminum compound and the sodium carbonate is replaced, for the precipitation and alkalinization steps, by potassium carbonate.

A catalyst charge of 500 g is introduced in a tubular reactor of 2.5 cm diameter and then reduced under the following conditions:
Pressure: 0.1 MPa
$H_2$ at 2% concentration by volume in nitrogen
VVH: 1500 $h^{-1}$ Temperature:
  10-hour steps at 140°, 160°, 180°, 210° and 240° C.; followed with
  2-hour steps at 300°, 350° and 400° C.

After 2 hours at 400° C. under the above-mentioned conditions, the temperature is decreased to 240° C.; the reactor is then purged and pressurized with nitrogen at 6 MPa. Nitrogen is then replaced with a synthesis gas $H_2+CO+CO_2$ having a molar ratio $H_2/CO=2$ and a 2% $CO_2$ content, while maintaining the temperature at 240° C. and the pressure at 6 MPa. The temperature is progressively increased to 280° C.; the pressure is maintained at 6 MPa; the synthesis gas flow rate is 3000 liters/liter of catalyst per hour (l/l/h). The contact between the catalyst and the synthesis gas is maintained, at these conditions, for about 300 hours.

The results obtained with of the catalyst at 300 hours are as follows:
  selectivity to alcohols: $S_A=67\%$
  alcohols productivity by weight: P=0.08 g/h/g of catalyst
  selectivity by weight to higher alcohols $C_2+OH$: $S_{C_2+OH}=43\%$ The synthesis is continued under the same conditions for 300 additional hours; the results at 600 hours are as follows:
  $S_A=66\%$
  $P=0.075$ g/h/g
  $S_{C_2+OH}=44\%$

EXAMPLE 9

A new test is performed with a new charge of the catalyst of example 8.

The reduction procedure is as follows:
  Pressure: 0.1 MPa
  $H_2$ at 2% concentration by volume in nitrogen
  $VVH=1500$ h$^{-1}$
  Temperature: 10-hour steps at 140°, 160°, 180°, 210° and 240° C.

After 10 hours at 240° C. in the above-mentioned conditions, the reactor is purged with nitrogen. The procedure of supplying synthesis gas and the test conditions are identical to those of example 8.

The results obtained with the catalyst at 300 hours are as follows:
  selectivity to alcohols: $S_A=68\%$
  alcohols productivity by weight: P=0.10 g/h/g of catalyst
  selectivity by weight to higher alcohols $C_2+OH$: $S_{C_2+OH}=33\%$ After 300 hours, the catalyst is placed under hydrogen according to the following procedure:

The temperature and pressure of the reactor are respectively decreased to 240° C. and 1 atmosphere (0.1 MPa), then the totality of the carbon monoxide flow and a part of the hydrogen flow are very quickly replaced with a nitrogen flow so that the hydrogen concentration in nitrogen be about 2% by volume. Then the temperature is progressively increased to 400° C. by 2-hour steps at 240°, 300°, 350° and 400° C. The reactor is then brought back to 240° C., purged with nitrogen and then pressurized with nitrogen at 6 MPa. Nitrogen is replaced with the synthesis gas ($H_2/CO=2$; 2% $CO_2$) and the reactor temperature is progressively brought to 280° C. Then the synthesis is performed again for 300 hours under the following conditions:

$P=6$ MPa; $T°=280°$ C.; $VVH=3000$ h$^{-1}$; $H_2/CO=2$; $CO_2=2\%$

The results obtained with the catalyst at 300 hours, after this new hydrogen treatment, are as follows:
  selectivity to alcohols: $S_A=75\%$
  alcohols productivity by weight: P=0.08 g/h/g of catalyst
  selectivity by weight to higher alcohols $C_2+OH$: $S_{C_2+OH}=45\%$ It is observed that the process for using catalysts according to the invention provides in particular for an improved selectivity to alcohols ($S_A$).

What is claimed as the invention is:

1. A process for synthesizing saturated primary aliphatic alcohols by reaction of carbon oxides (CO, $CO_2$) with hydrogen, in the presence of copper and cobalt-containing catalysts, characterized by the following successive steps:

(a) a first step wherein said catalyst is subjected to at least one prereduction, said catalyst prereduction being performed by contact with a gas mixture containing at least one inert gas and at least one reducing gas in a molar ratio "reducing gas/reducing gas+inert gas" from about 0.001:1 to 1:1, said reducing gas being selected from the group consisting of hydrogen and carbon monoxide, said prereduction being conducted at a temperature from about 100° C. to about 750° C., with a hourly volumetric velocity of the gas mixture from about $10^2$ to about $4.10^4$ hour$^{-1}$, under a total pressure from about 0.1 to about 10 MPa and with a reducing gas partial pressure at most equal to 1 MPa, (b) a second step wherein said prereduced catalyst is contacted with a synthesis gas containing hydrogen and carbon oxides (CO, $CO_2$) in a molar ratio $H_2/CO+CO_2$ from about 0.4 to about 10, under a total pressure from about 2 to about 15 MPa with a partial pressure of the hydrogen-carbon monoxide mixture of at least 2 MPa, at a temperature from about 240° to about 350° C. during at least about 10 hours, with a hourly volumetric velocity of said synthesis gas from about $15.10^2$ to about $6.10^4$ hour$^{-1}$ so as to produce a mixture of saturated primary aliphatic alcohols containing higher alcohols, (c) a third step wherein the catalyst obtained in the second step is subjected to a treatment with a gas mixture containing a single reducing gas and at least one inert gas in a molar ratio "reducing gas/reducing gas+inert gas" from about 0.01 to 1/1 said single reducing gas being selected from the group consisting of hydrogen and carbon monoxide, said treatment being performed at a temperature from about 200° to 750° C., under a pressure from about 0.1 to about 10 MPa, during about 1 to about 400 hours and with a hourly volume velocity of the gas mixture from about $10^2$ to about $4.10^4$ hour$^{-1}$.

(d) a fourth step of synthesizing a mixture of saturated primary aliphatic alcohols containing higher alcohols, wherein the catalyst obtained in the third step is contacted with a synthetic gas containing hydrogen and carbon oxides (CO, $CO_2$) in a molar ratio $H_2/CO+CO_2$ from about 0.4 to about 10, under a pressure from about 2 to about 25 MPa, at a temperature from about 240° to about 400° C. and with a hourly volume velocity of said synthetic gas from about $15.10^2$ to about $6.10^4$ hour$^{-1}$.

2. A process according to claim 1, wherein the first step consists of a single prereduction at a temperature from about 120° to about 250° C. by means of a gas mixture containing at least one inert gas and hydrogen in a molar ratio "hydrogen/hydrogen+inert gas" from about 0.01:1 to about 0.1:1, under a total pressure from about 0.1 to about 10 MPa and a hydrogen partial pressure at most equal to about 1 MPa and with a hourly volumetric velocity of the gas mixture from about $10^2$ to about $4.10^4$ hour$^{-1}$.

3. A process according to claim 1, wherein the first step comprises two successive prereductions performed under a total pressure from about 0.1 to about 10 MPa, with a reducing gas partial pressure at most equal to about 1 MPa and with a hourly volumetric velocity of the gas mixture from about $10^2$ to about $4.10^4$ hour$^{-1}$, the first prereduction being performed at a temperature from about 120° to about 250° C. with a gas mixture having a molar ratio "reducing gas/reducing gas+inert gas" from about 0.001:1 to about 0.1:1, the second prereduction being then performed at a temperature from about 220° C. to about 750° C. with a gas mixture having a molar ratio "reducing gas/reducing gas+inert gas" from about 0.01:1 to 1:1, said second prereduction being performed in more severe conditions, as a whole, than the first prereduction.

4. A process according to claim 1, wherein the second step is performed for a time of about 50 to about 1000 hours.

5. A process according to claim 1, wherein the second step is continued until the catalyst has lost at least partially its productivity and/or selectivity to alcohols and/or selectivity to higher alcohols.

6. A process according to claim 1, wherein the third step is performed for about 10 to about 200 hours, with a gas mixture containing a single reducing gas and at least one inert gas in a molar ratio "reducing gas/reducing gas+inert gas" from about 0.02:1 to 1:1, at a temperature from about 240° to about 600° C., under a pressure from about 0.1 to about 6 MPa and with a hourly volumetric velocity of said gas mixture from about $5.10^2$ to about $2.10^4$ hour$^{-1}$.

7. A process according to claim 1, wherein hydrogen is used as the single reducing gas in the third step.

8. A process according to claim 1, wherein the catalyst having at least partially lost its productivity and/or selectivity to alcohols and/or selectivity to higher alcohols at the end of the fourth step is subjected to a new treatment with a gas mixture containing a single reducing gas and at least one inert gas, under the conditions defined for the third step in claim 1, said catalyst being used at the end of this new treatment in a new synthesis step under the conditions defined for the fourth step in claim 1.

9. A process according to claim 1, wherein the catalyst, in addition to copper and cobalt, optionally contains aluminum, zinc, at least one metal M selected from the group consisting of manganese, vanadium, iron and rhenium, at least one metal N selected from the group consisting of scandium, yttrium, thorium, zirconium and the rare-earth metals of atomic numbers from 57 to 71 included, chromium and at least one alkali and/or alkaline-earth metal A selected from the group consisting of lithium, sodium, potassium, rubidium, cesium, beryllium, magnesium, calcium, strontium and barium, the amount by weight of each metal element in proportion to the total metals weight being:

| Copper | 8–70% |
|---|---|
| Cobalt | 3–55% |
| Aluminum | 0–45% |
| Zinc | 0–70% |
| A metal | 0–18% |
| M metal | 0–20% |
| N metal | 0–60% |
| Chromium | 0–15% | the atomic ratio between these metals being:

| Cu/Co | 0.05–10 |
|---|---|
| Al/Co | 0–5 |
| Zn/Co | 0–10 |
| A metals/Co | 0–3.5 |
| M metals/Co | 0–1 |
| Cr/Co | 0–1 |
| N metals/Co | 0–2 |

10. A process according to claim 9, wherein the catalyst contains copper, cobalt, aluminum, zinc and sodium, the proportion by weight of each metal element with respect to the total metals weight being:

| Copper | 10–65% |
|---|---|
| Cobalt | 5–50% |
| Aluminum | 5–40% |
| Sodium | 0.2–10% |
| Zinc | 5–50% | and the atomic ratios between these metals being:

| Cu/Co | 0.1–5 |
|---|---|
| Al/Co | 0.7–4 |
| Na/Co | 0.05–1.5 |
| Zn/Co | 0.1–5 |

* * * * *